(12) United States Patent
Parthasaradhi Reddy et al.

(10) Patent No.: US 8,466,279 B2
(45) Date of Patent: Jun. 18, 2013

(54) POLYMORPHS OF EFAVIRENZ

(75) Inventors: Bandi Parthasaradhi Reddy, Hyderabad (IN); Kura Rathnakar Reddy, Hyderabad (IN); Rapolu Raji Reddy, Hyderabad (IN); Dasari Muralidhara Reddy, Hyderabad (IN); Kesireddy Subash Chander Reddy, Hyderabad (IN)

(73) Assignee: Hetero Drugs Limited (IN)

( * ) Notice: Subject to any disclaimer, the term of this patent is extended or adjusted under 35 U.S.C. 154(b) by 0 days.

(21) Appl. No.: 13/540,987

(22) Filed: Jul. 3, 2012

(65) Prior Publication Data

US 2012/0271047 A1 Oct. 25, 2012

Related U.S. Application Data

(60) Division of application No. 13/174,893, filed on Jul. 1, 2011, now Pat. No. 8,242,267, which is a continuation of application No. 10/568,904, filed as application No. PCT/IN2004/000250 on Aug. 19, 2004, now abandoned.

(51) Int. Cl.
*C07D 265/18* (2006.01)

(52) U.S. Cl.
USPC ............................... 544/92; 514/230.5

(58) Field of Classification Search
USPC .................................................. 544/92
See application file for complete search history.

(56) References Cited

U.S. PATENT DOCUMENTS

| | | | |
|---|---|---|---|
| 5,519,021 A * | 5/1996 | Young et al. | 514/230.5 |
| 5,665,720 A | 9/1997 | Young et al. | |
| 6,090,821 A * | 7/2000 | Patel et al. | 514/312 |
| 6,639,071 B2 * | 10/2003 | Crocker et al. | 544/92 |
| 7,074,811 B2 | 7/2006 | Craig | |
| 7,825,125 B2 | 11/2010 | Stritzke et al. | |
| 7,897,613 B2 | 3/2011 | Arul et al. | |
| 8,114,900 B2 | 2/2012 | Ini et al. | |
| 8,134,008 B2 | 3/2012 | Reddy et al. | |
| 8,258,296 B2 | 9/2012 | Paredes et al. | |
| 2004/0102523 A1 | 5/2004 | Broquaire et al. | |

FOREIGN PATENT DOCUMENTS

| | | |
|---|---|---|
| WO | 9833782 | 8/1998 |
| WO | 9964405 | 12/1999 |
| WO | 2006018853 | 2/2006 |

OTHER PUBLICATIONS

Banga S, Chawla G, Bansal AK; "New trends in crystallization of active pharmaceutical ingredients"; Business Briefing: Pharmagenerics; pp. 2-3, Nov. 1-5, 2004.
U.S. Appl. No. 09/282,744, filed Mar. 31, 1999, 1.132 Declaration of Louis S. Crocker; 12 pages, signed May 23, 2001.
International Search Report; International Application No. PCT/IN2004/000250; International Filing Date Aug. 19, 2004; Date of Mailing Feb. 23, 2006; 4 pages.
Pierce, et al.; "Practical Asymmetric Synthesis of Efavirenz (DMP 266), an HIV-1 Reverse Transcriptase Inhibitor"; J. Org. Chem; 63; pp. 8536-8543; (1998).
Radesca, et al.; "Hynthesis of HIV-1 Reverse Transcriptase Inhibitor DMP 266"; Synthetic Communication; 27(24); pp. 4373-4384; (1997).
Sustiva Package Insert; Princeton, New Jersey: Bristol-Myers Squibb Co., 2005.
United States Pharmacopeia—National Formulary (USP25 NF20), 2002, pp. 2088-2089.

* cited by examiner

*Primary Examiner* — Kahsay T Habte
(74) *Attorney, Agent, or Firm* — Cantor Colburn LLP

(57) ABSTRACT

The present invention relates to novel amorphous and crystalline forms of efavirenz, processes for their preparation and pharmaceutical compositions containing them. In accordance with the present invention efavirenz crude is dissolved in acetone at 25° C.-30° C., the solution is slowly added to water for 30 minutes at 0° C.-5° C., stirred for 1 hour at the same temperature, the separated solid is filtered, washed with water and dried at 55° C.-60° C. for 5 hours to give amorphous efavirenz.

13 Claims, 2 Drawing Sheets

POLYMORPHS OF EFAVIRENZ

CROSS-REFERENCE TO RELATED APPLICATIONS

This application is a divisional of U.S. application Ser. No. 13/174,893 filed on Jul. 1, 2011, which is a continuation of U.S. patent application Ser. No. 10/568,904, filed on Feb. 17, 2006, which is a 371 of PCT/IN2004/000250, filed on Aug. 19, 2004, which is incorporated by reference herein in its entirety.

FIELD OF THE INVENTION

The present invention relates to novel polymorphs of efavirenz, processes for their preparation and pharmaceutical compositions containing them.

BACKGROUND OF THE INVENTION

The present invention relates to novel polymorphs of efavirenz, processes for their preparation and pharmaceutical compositions containing them.

Pharmaceutical products with HIV reverse transcriptase (including its resistant varieties) inhibitors are described in U.S. Pat. No. 5,519,021. An especially important compound among those disclosed is efavirenz, (4S)-6-chloro-4-(cyclopropylethynyl)-1,4-dihydro-4-(trifluoromethyl)-2H-3,1-benzoxazin-2-one. Efavirenz has the following structural formula:

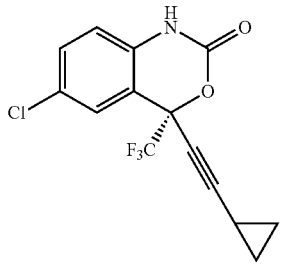 [SMILES: O=C1Nc2ccc(Cl)cc2[C@@](C#CC2CC2)(C(F)(F)F)O1]

This compound is used for the preparation of a medicament having nonnucleoside HIV-1 reverse transcriptase inhibiting activity that is useful in the prevention or treatment of infection by HIV and the treatment of AIDS. Efavirenz is sold commercially as SUSTIVA® by Bristol Myers Squibb.

WO patent application publication No. 98/33782 disclosed three crystalline forms, Form I (characterized by an x-ray powder diffraction patterns having peaks expressed as 2θ at 6.1, 6.4, 10.4, 10.9, 12.3, 13.2, 14.2, 15.2, 16.9, 18.4, 19.2, 20.1, 21.2, 22.3, 23.0, 24.9, 25.9, 26.3, 27.2, 28.1, 28.6, 29.1, 29.5, 30.7, 32.4 and 38.3 degrees), Form II (characterized by an x-ray powder diffraction patterns having peaks expressed as 2θ at 3.6, 6.3, 11.1, 12.8, 13.3, 14.3, 16.1, 16.9, 18.5, 19.2, 19.6, 20.6, 21.3, 22.6, 23.2, 24.4, 24.9, 26.0, 26.8, 27.6, 28.4, 29.2, 29.6, 30.6, 31.9 and 33.8 degrees) and Form III (characterized by an x-ray powder diffraction patterns having peaks expressed as 2θ at 7.2, 10.9, 13.7, 14.5, 16.7, 19.1, 19.6, 20.8, 21.7, 22.3, 22.8, 23.2, 23.9, 24.5, 24.9, 25.8, 27.0, 27.6, 29.3, 30.3, 30.7, 31.3, 33.4, 38.4 and 39.2 degrees) of efavirenz.

WO patent application publication No. 99/64405 disclosed five crystalline forms, Form 1 (characterized by an x-ray powder diffraction patterns having peaks expressed as 2θ at about 6.0, 6.3, 10.3, 10.8, 14.1, 16.8, 20.0, 20.5, 21.1 and 24.8 degrees), Form 2 (characterized by an x-ray powder diffraction patterns having peaks expressed as 2θ at about 6.8, 9.2, 12.3, 16.2, 21.4, 22.7, 24.1 and 28.0 degrees), Form 3 (characterized by an x-ray powder diffraction patterns having peaks expressed as 2θ at about 7.1, 7.3, 11.0, 13.8, 20.9, 23.3, 27.9 and 33.5 degrees), Form 4 (characterized by an x-ray powder diffraction patterns having peaks expressed as 2θ at about 3.6, 6.3, 9.7, 11.0, 12.7, 13.2, 16.1, 19.2, 19.5, 20.6 and 24.3 degrees) and Form 5 (characterized by an x-ray powder diffraction patterns having peaks expressed as 2θ at about 10.2, 11.4, 11.6, 12.6, 19.1, 20.6, 21.3, 22.8, 24.8, 27.4, 28.2 and 31.6 degrees) of efavirenz.

We have discovered a stable novel crystalline form of efavirenz. The novel form is at least as stable as the reported forms (Form I, Form II, Form III, Form 1, Form 2, Form 3, Form 4 and Form 5). The novel crystalline form is stable over the time and has good flow properties and so, the novel crystalline form is suitable for formulating efavirenz.

Amorphous form of efavirenz has not been reported in the prior art. So, there is a need for stable amorphous form of efavirenz for better pharmaceutical preparations.

One object of the present invention is to provide a stable novel crystalline form of efavirenz, process for preparing it and a pharmaceutical composition containing it.

Another object of the present invention is to provide a novel stable amorphous form of efavirenz, process for preparing it and a pharmaceutical composition containing it.

DETAILED DESCRIPTION OF THE INVENTION

In accordance with the present invention, there is provided a novel amorphous form of efavirenz. The amorphous efavirenz is characterized by having broad x-ray diffraction spectrum as in FIG. 1.

In accordance with the present invention, a process is provided for preparation of amorphous efavirenz, which comprises:

precipitating from a solution of efavirenz in a $C_3$-$C_8$-ketonic solvent by using water as precipitating solvent at below about 15° C., and collecting the precipitated solid; and drying the solid collected at about 40° C.-65° C. to obtain amorphous efavirenz.

The preferable ketonic solvent is selected from acetone, methyl ethyl ketone, methyl isobutyl ketone, methyl tert-butyl ketone and diethyl ketone; more preferable ketonic solvent is selected from acetone and diethyl ketone; and still more preferable ketonic solvent is acetone.

The solution of efavirenz in the ketonic solvent may be prepared by dissolving efavirenz in a known form or in crystalline form H1 described below in the said ketonic solvent. Alternatively, crude efavirenz may also be used in the process.

Preferably the precipitation is carried out at about 0° C.-10° C. and more preferably at about 2° C.-5° C.

The precipitated solid may be collected by filtration or centrifugation.

The preferable temperature range of drying is at about 50° C.-60° C. and more preferable temperature range is at about 55° C.-60° C.

Preferably the process is carried out by precipitating from a solution of efavirenz in a $C_3$-$C_8$-ketonic solvent, preferably acetone, by adding the said solution to water at about 0° C.-10° C. and more preferably at about 2° C.-5° C.; collecting the precipitated solid by filtration or centrifugation; and drying the solid collected at about 40° C.-65° C., more preferably at about 55° C.-60° C. to obtain amorphous efavirenz.

The novel amorphous efavirenz is found to have better dissolution properties when compared with the known forms.

In accordance with the present invention, there is provided a novel crystalline form of efavirenz, designated as form H1, characterized by an x-ray powder diffraction spectrum having peaks expressed as 2θ at about 5.4, 10.4, 11.6, 12.5, 15.3, 20.1, 20.8, 22.5, 23.1, 25.7, 27.9, 28.5, 28.8, 29.5, 30.2 and 38.2 degrees. FIG. 2 shows typical form H1 x-ray powder diffraction spectrum.

In accordance with the present invention, a process is provided for preparation of efavirenz form H1, which comprises:
a) precipitating from a solution of efavirenz in a $C_1$-$C_6$-alcoholic, $C_3$-$C_8$-ketonic solvent or a mixture thereof by using water as precipitating solvent at below about 15° C., collecting the precipitated solid;
b) drying the solid collected at about 25° C.-35° C. until the water content falls in the range 2-10% of the solid by weight; and
c) drying the solid obtained in (b) at about 40° C.-55° C. to obtain crystalline efavirenz form H1.

The preferable alcoholic solvent is selected from ethanol, n-propanol, n-butanol, isopropanol and methanol and more preferable alcoholic solvent is n-propanol.

The preferable ketonic solvent is selected from acetone, methyl ethyl ketone, methyl isobutyl ketone, methyl tert-butyl ketone and diethyl ketone; more preferable ketonic solvent is selected from acetone and diethyl ketone; and still more preferable ketonic solvent is acetone.

The solution of efavirenz in the ketonic or alcoholic solvent may be prepared by dissolving efavirenz in a known form or in amorphous form in the said ketonic or alcoholic solvent. Alternatively, crude efavirenz may also be used in the process.

Preferably the precipitation is carried out at about 0° C.-10° C. and more preferably at about 2° C.-5° C.

The precipitated solid may be collected by filtration or centrifugation.

It has been found that the drying of precipitated product in step (a) directly at higher temperature leads to known crystalline form 1 (WO patent application publication No. 99/64405).

Preferably the drying in step (b) is carried out until the water content falls in the range 2-5% of the solid by weight.

The preferable temperature range of drying in step (c) is at about 40° C.-50° C. and more preferably at about 40° C.-45° C.

Preferably the process is carried out by precipitating from a solution of efavirenz in a $C_1$-$C_6$-alcoholic solvent, preferably n-propanol or isopropanol, $C_3$-$C_8$-ketonic solvent, preferaly acetone or diethyl ketone, or a mixture thereof by adding the said solution to water at about 0° C.-10° C. and more preferably at about 2° C.-5° C.; collecting the precipitated solid by filtration or centrifugation; drying the precipitated solid at about 25° C.-35° C. until the water content is 2-5%; and drying the solid obtained at about 40° C.-55° C., preferably at about 40° C.-50° C., to obtain crystalline efavirenz form H1.

Unless otherwise specified, the alkyl portion of the $C_1$ to $C_5$-alcohol and $C_3$ to $C_8$-ketone used can be straight or branch, unsubstituted or substituted with for example alkoxy, halogen, nitro, cyano or hydroxy groups.

The novel crystalline efavirenz form H1 is at least as stable as the reported forms (Form I, Form II, Form III, Form 1, Form 2, Form 3, Form 4 and Form 5). The novel crystalline form is stable over the time and has good flow properties and so, the novel crystalline form is suitable for formulating efavirenz.

The above novel polymorphs of efavirenz are useful for the preparation of medicaments having nucleoside HIV-1 reverse transcriptase inhibiting activity that is useful in the prevention or treatment of infection by HIV and the treatment of aids. The novel polymorphs of efavirenz can be used in pharmaceutical compositions generally in combination with at least one pharmaceutically acceptable excipient.

All the patents mentioned above are incorporated herein by reference.

Figure 1:
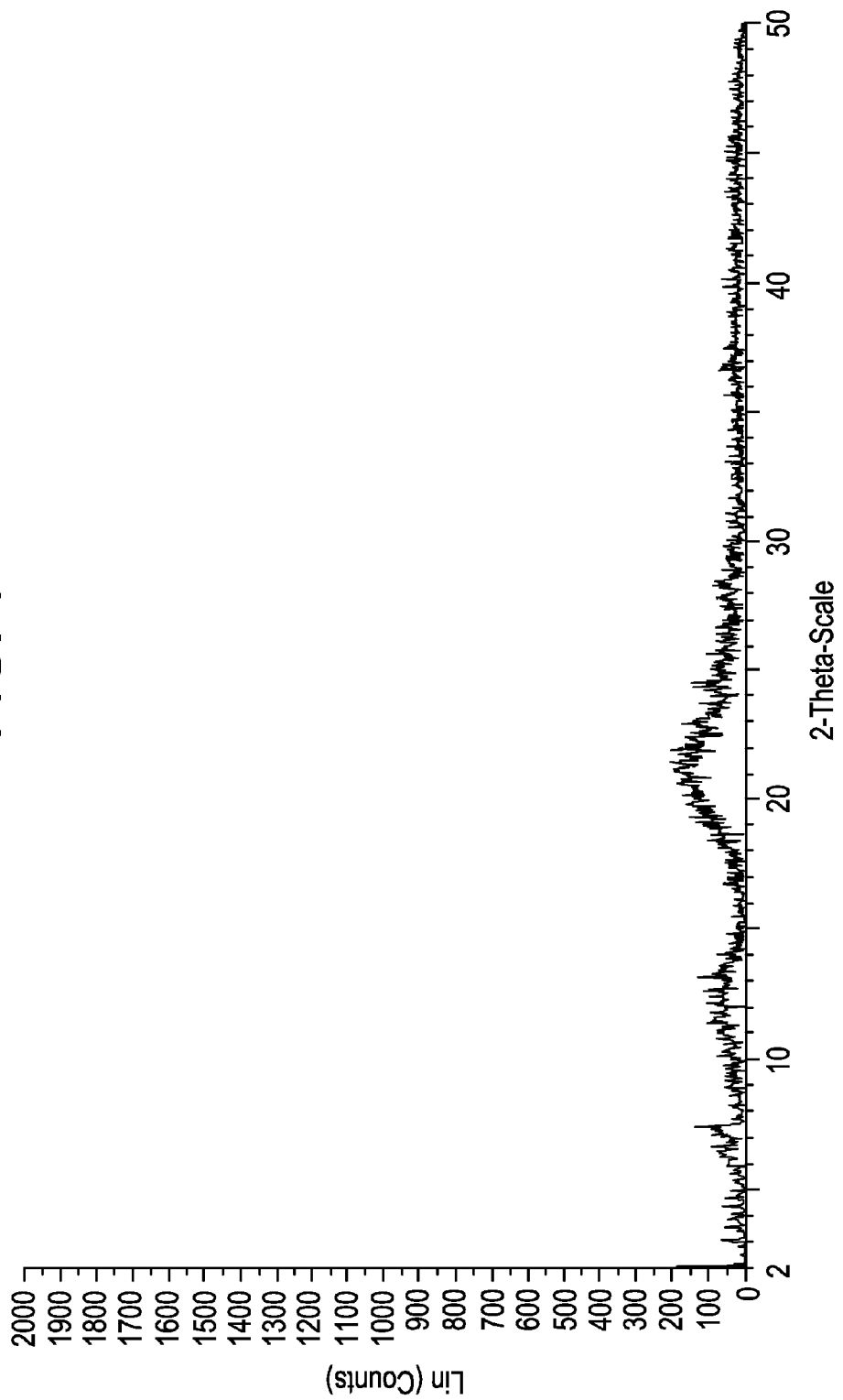
FIG. 1 is a x-ray powder diffraction spectrum of amorphous form of efavirenz.
Figure 2:
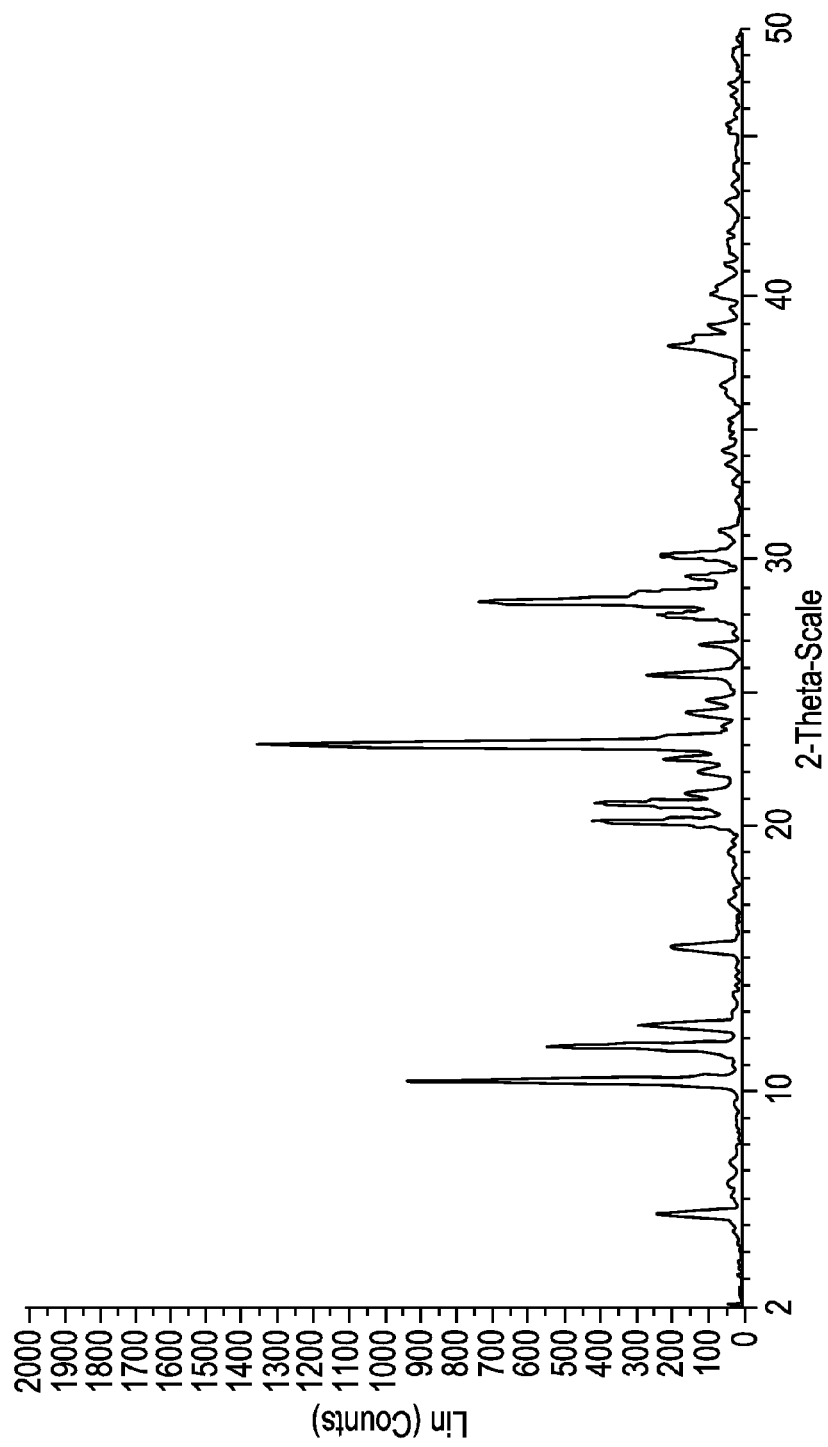
FIG. 2 is a x-ray powder diffraction spectrum of efavirenz form H1.

x-Ray powder diffraction spectrum was measured on a Bruker axs D8 advance x-ray powder diffractometer having a copper-Kα radiation.

The following examples are given for the purpose of illustrating the present invention and should not be considered as limitations on the scope or spirit of the invention.

EXAMPLE 1

Efavirenz crude (5 gm, obtained by the process described in example 6, step A to step D, of U.S. Pat. No. 5,519,021) is dissolved in acetone (20 ml) at 25° C.-30° C., slowly added to water (200 ml) for 30 minutes at 0° C.-5° C. and stirred for 1 hour at the same temperature. Then the separated solid is filtered, washed with water (20 ml) and dried at 55° C.-60° C. for 5 hours to give 4.5 gm of amorphous efavirenz.

EXAMPLE 2

Efavirenz form 1 (10 gm, obtained by the process described in example 8 of WO patent application publication No. 99/64405) is dissolved in diethylketone (50 ml) at 25° C.-30° C., slowly added to water (350 ml) for 45 minutes at 0° C.-5° C. and stirred for 2 hours at the same temperature. Then the separated solid is filtered, washed with water (50 ml) and dried at 55° C.-60° C. for 5 hours to give 9.5 gm of amorphous efavirenz.

EXAMPLE 3

Efavirenz crude (5 gm) is dissolved in n-propanol (20 ml) at 25° C.-30° C., slowly added to water (200 ml) for 30 minutes at 0° C.-5° C. and stirred for 1 hour at the same temperature. Then the separated solid is filtered, washed with water (20 ml) and dried at 25° C.-30° C. for 18 hours to obtain efavirenz as wet solid (moisture content: 2.5% by Karl fisher method). The wet solid is dried at 40° C.-45° C. to give 4.4 gm of efavirenz form H1 (water content: 0.3%).

EXAMPLE 4

Amorphous efavirenz (5 gm, obtained in example 1) is dissolved in isopropanol (25 ml) at 25° C.-30° C., slowly added to water (170 ml) for 30 minutes at 0° C.-5° C. and stirred for 1 hour 30 minutes at the same temperature. Then the separated solid is filtered, washed with water (30 ml) and dried at 25° C.-30° C. for 20 hours to obtain efavirenz as wet solid (moisture content: 3.2% by Karl fisher method). The wet solid is dried at 40° C.-45° C. to give 4.3 gm of efavirenz form H1 (water content: 0.35%).

We claim:

1. Amorphous efavirenz.
2. Amorphous efavirenz according to FIG. 1.
3. A process for preparation of amorphous efavirenz, comprising:
   a) precipitating efavirenz from a solution of efavirenz in a $C_3$-$C_8$-ketonic solvent by adding water as a precipitating solvent at a temperature below 15° C., and collecting a precipitated solid to provide a collected solid; and
   b) drying the collected solid at a temperature of 40° C.-65° C. to provide amorphous efavirenz.
4. The process of claim 3, wherein the $C_3$-$C_8$ ketonic solvent is selected from the group consisting of acetone, methyl ethyl ketone, methyl isobutyl ketone, methyl tert-butyl ketone, and diethyl ketone.
5. The process of claim 4, wherein the $C_3$-$C_8$ ketonic solvent is selected from the group consisting of acetone and diethyl ketone.
6. The process of claim 5, wherein the $C_3$-$C_8$ ketonic solvent is acetone.
7. The process of claim 3, wherein the precipitation in step (a) is carried out at a temperature of 0° C.-10° C.
8. The process of claim 7, wherein the precipitation is carried out at a temperature of 2° C.-5° C.
9. The process of claim 3, wherein the temperature of drying in step b) is 50° C.-60° C.
10. The process of claim 9, wherein the temperature of drying is in step b) 55° C.-60° C.
11. The process of claim 3, wherein the process is carried out by precipitating efavirenz from a solution of efavirenz in a $C_3$-$C_8$-ketonic solvent by adding the solution to water at a temperature of 0° C.-10° C., collecting the precipitated solid by filtration or centrifugation and drying the collected solid at a temperature of 40° C.-65° C. to provide amorphous efavirenz.
12. The process of claim 11, wherein the ketonic solvent is acetone, the precipitation is carried out at a temperature of 2° C.-5° C. and drying is carried out at a temperature of 55° C.-60° C.
13. The amorphous efavirenz of claim 1, characterized by broad maxima in the powder x-ray diffraction pattern centered around 12 and 21 degrees two-theta.

* * * * *